(12) United States Patent
Shaw

(10) Patent No.: US 10,575,831 B2
(45) Date of Patent: Mar. 3, 2020

(54) FORENSIC ENCLOSURE FOR SECURE TAGGING AND RETENTION OF A DECEDENT HAND/LIMB FOR PURPOSES OF PRESERVING DNA AND FINGERPRINTS FOR TESTING IN ASSOCIATION WITH LEGAL OR MEDICAL PROCEEDINGS

(71) Applicant: Raymond R. Shaw, Farmington Hills, MI (US)

(72) Inventor: Raymond R. Shaw, Farmington Hills, MI (US)

( * ) Notice: Subject to any disclaimer, the term of this patent is extended or adjusted under 35 U.S.C. 154(b) by 358 days.

(21) Appl. No.: 15/640,925

(22) Filed: Jul. 3, 2017

(65) Prior Publication Data

US 2018/0000464 A1 Jan. 4, 2018

Related U.S. Application Data

(60) Provisional application No. 62/357,560, filed on Jul. 1, 2016.

(51) Int. Cl.
*A61B 10/00* (2006.01)

(52) U.S. Cl.
CPC .............................. *A61B 10/0096* (2013.01)

(58) Field of Classification Search
CPC ... A61B 10/0096; A61B 10/0038; B01L 3/50; B01L 3/505; G01N 33/48
USPC ..... 73/964.91, 864.51, 864.62; 27/1, 19, 20; 220/2.1 R, 592.12–592.28, 9.1–9.4, 305, 220/315, 319, 320; 215/273, 274, 285, 215/286, 352; 206/231, 236, 265, 271
See application file for complete search history.

(56) References Cited

U.S. PATENT DOCUMENTS

| | | | | |
|---|---|---|---|---|
| 2,138,975 A | * | 12/1938 | Malik | A61F 5/05841 602/16 |
| 3,774,798 A | * | 11/1973 | Andrade | G09F 3/037 215/291 |
| 4,265,049 A | * | 5/1981 | Gorewitz | A01G 13/043 47/29.1 |
| 5,027,799 A | * | 7/1991 | Laico | A61G 13/12 5/623 |
| 5,211,667 A | * | 5/1993 | Danforth | A61F 2/7812 623/33 |

(Continued)

FOREIGN PATENT DOCUMENTS

| | | | |
|---|---|---|---|
| CH | 637821 | * | 8/1983 |
| CN | 2724664 | * | 9/2005 |
| FR | 2553657 | * | 4/1985 |

*Primary Examiner* — Robert R Raevis
(74) *Attorney, Agent, or Firm* — Dinsmore & Shohl LLP

(57) ABSTRACT

An evidence retaining enclosure for receiving a limb for purposes of retaining DNA evidence and the like. The enclosure includes an elongated body having a first open end and a second closed end, with the limb adapted to being inserted into the open end such that an end thereof is retained in proximity to the closed end. At least one pair of circumferential extending straps are associated with the open end for sizing about a projecting dimension of the limb, the straps being inter-engaged in order to secure the enclosure in place. The body further includes first and second telescoping portions, the first portion integrating the closed end and the second portion integrating the circumferential straps. Axial fixing straps extend between the first and second telescoping portions for fixing an inter-telescoping relationship established therebetween.

15 Claims, 12 Drawing Sheets

(56) References Cited

U.S. PATENT DOCUMENTS

| | | |
|---|---|---|
| 7,484,275 B2 | 2/2009 | Carroll et al. |
| 8,869,360 B1 | 10/2014 | Smith |
| 8,966,727 B1 | 3/2015 | Green et al. |
| 8,991,019 B1 | 3/2015 | Calvert |
| 2005/0278039 A1* | 12/2005 | Nobbe ............... A61F 2/7812 623/31 |
| 2008/0277393 A1* | 11/2008 | True ................... B65D 77/06 220/9.4 |
| 2009/0030353 A1* | 1/2009 | Bonutti ............... A61F 5/013 601/5 |
| 2009/0260638 A1* | 10/2009 | Duplessie ............ A41D 19/01 128/879 |
| 2009/0294455 A1* | 12/2009 | Pruchnicki ........... A45C 11/20 220/592.2 |
| 2011/0197336 A1* | 8/2011 | Suk ................ A41D 19/01582 2/161.3 |
| 2013/0174392 A1 | 7/2013 | Chua et al. |
| 2013/0341338 A1* | 12/2013 | Mitchell ............. A45C 11/20 220/592.2 |
| 2014/0259577 A1 | 9/2014 | Richardson |
| 2014/0267116 A1* | 9/2014 | Weiner .............. A61F 5/05866 345/173 |
| 2015/0203288 A1* | 7/2015 | Hunter ............. B65D 88/1668 222/1 |
| 2015/0314956 A1* | 11/2015 | Clevenger ........... B65F 1/1405 220/9.2 |
| 2015/0335455 A1* | 11/2015 | Sorrenti ............. A61F 5/0102 602/16 |
| 2016/0100706 A1* | 4/2016 | Pidwell .............. A45C 11/00 220/9.1 |

* cited by examiner

FORENSIC ENCLOSURE FOR SECURE TAGGING AND RETENTION OF A DECEDENT HAND/LIMB FOR PURPOSES OF PRESERVING DNA AND FINGERPRINTS FOR TESTING IN ASSOCIATION WITH LEGAL OR MEDICAL PROCEEDINGS

CROSS REFERENCE TO RELATED APPLICATIONS

The present application claims the priority of U.S. Ser. No. 62/357,560 filed Jul. 1, 2016.

BACKGROUND OF THE INVENTION

Field of the Invention

The present invention discloses an evidence enclosure for supporting a limb, typically belonging to a deceased suspect or criminal, and which can include a forearm and hand providing DNA or fingerprint evidence such as may be associated with a criminal proceeding. The limb enclosure provides stand-offs for spacing above a ground surface, as well as circumferential extending and adjustable attachments at one end for securing about an end location of the decedent's limb (e.g. elbow and/or forearm). A fabric covering with an open inserting and drawstring closing end is provided for sealing the limb once inserted axially within the evidence enclosure in a direction towards its closed opposite end.

Description of the Prior Art

The prior art is documented with examples of remains transport devices and enclosures, the most typical of which is the standard zippered body bag. For purposes of DNA retention and evidence gathering, such as at a crime scene, conventional bags are unsuitable for retention of human remains (and in particular a decedent's limbs which may include evidentiary valuable DNA or the like) in such a manner which the DNA and evidentiary integrity of the remains/limbs are preserved.

Other examples from the prior art include the gas-tight, liquid-impervious, transportable contaminated remains pouch of Carroll U.S. Pat. No. 7,484,275, the body bag of Smith U.S. Pat. No. 8,869,360 and the contaminated human remains pouch of Green U.S. Pat. No. 8,966,727. Additional references of note include the crime-scene body bag of U.S. Pat. No. 8,991,019 to Calvert, the closable container of Richardson US 2014/0259577 for holding human remains and including a filtration unit and the body bag with absorbent lining disclosed in US 2013/0174392 of Chua et al.

SUMMARY OF THE PRESENT INVENTION

The present invention discloses an evidence retaining enclosure for receiving a limb for purposes of retaining DNA evidence and the like and includes an elongated body having a first open end and a second closed end, with the limb adapted to being inserted into the open end such that an end thereof is retained in proximity to the closed end. At least one pair of circumferential extending straps are associated with the open end for sizing about a projecting dimension of the limb, the straps being inter-engaged in order to secure the enclosure in place.

The body further includes first and second telescoping portions, the first portion integrating the closed end and the second portion integrating the circumferential straps. Axial fixing straps extending between the first and second telescoping portions for fixing an inter-telescoping relationship established therebetween. Additional features include comprising circumferential rim extending stand-offs associated with each of the first and second telescoping portions.

An elongated and sleeve shaped fabric is attached to the enclosure at a first end and is adapted to be extended in order to cover a portion of the limb extending from the enclosure, a drawstring at the end of the fabric tightening to enclose around the limb. Each of the circumferential extending straps and the axial extending fixing straps may further include peel away adhesive undersides. The body further can also include a Kraft paper or corrugated paperboard construction and can also exhibit a polygonal cross sectional profile.

BRIEF DESCRIPTION OF THE DRAWINGS

Reference will now be made to the attached drawings, when read in combination with the following detailed description, wherein like reference numerals refer to like parts throughout the several views, and in which.

DETAILED DESCRIPTION OF THE PREFERRED EMBODIMENTS

With referenced to the attached illustrations, the present invention discloses an evidence enclosure for supporting a limb, typically belonging to a deceased suspect or criminal, and which can include a forearm and hand providing DNA or fingerprint evidence such as may be associated with a criminal proceeding, one aspect of the enclosure being not only to protect the evidence from contamination but to also protect the same from falling off or being otherwise dislodged from the hand. As will be further described, the limb enclosure provides stand-offs for spacing above a ground surface, as well as circumferential extending and adjustable attachments at one end for securing about an end location of the decedent's limb (e.g. elbow and/or forearm). As will also be described, the fabric covering with an open inserting and drawstring closing end is provided for sealing the limb once inserted axially within the evidence enclosure in a direction towards its closed opposite end.

Figure 1:
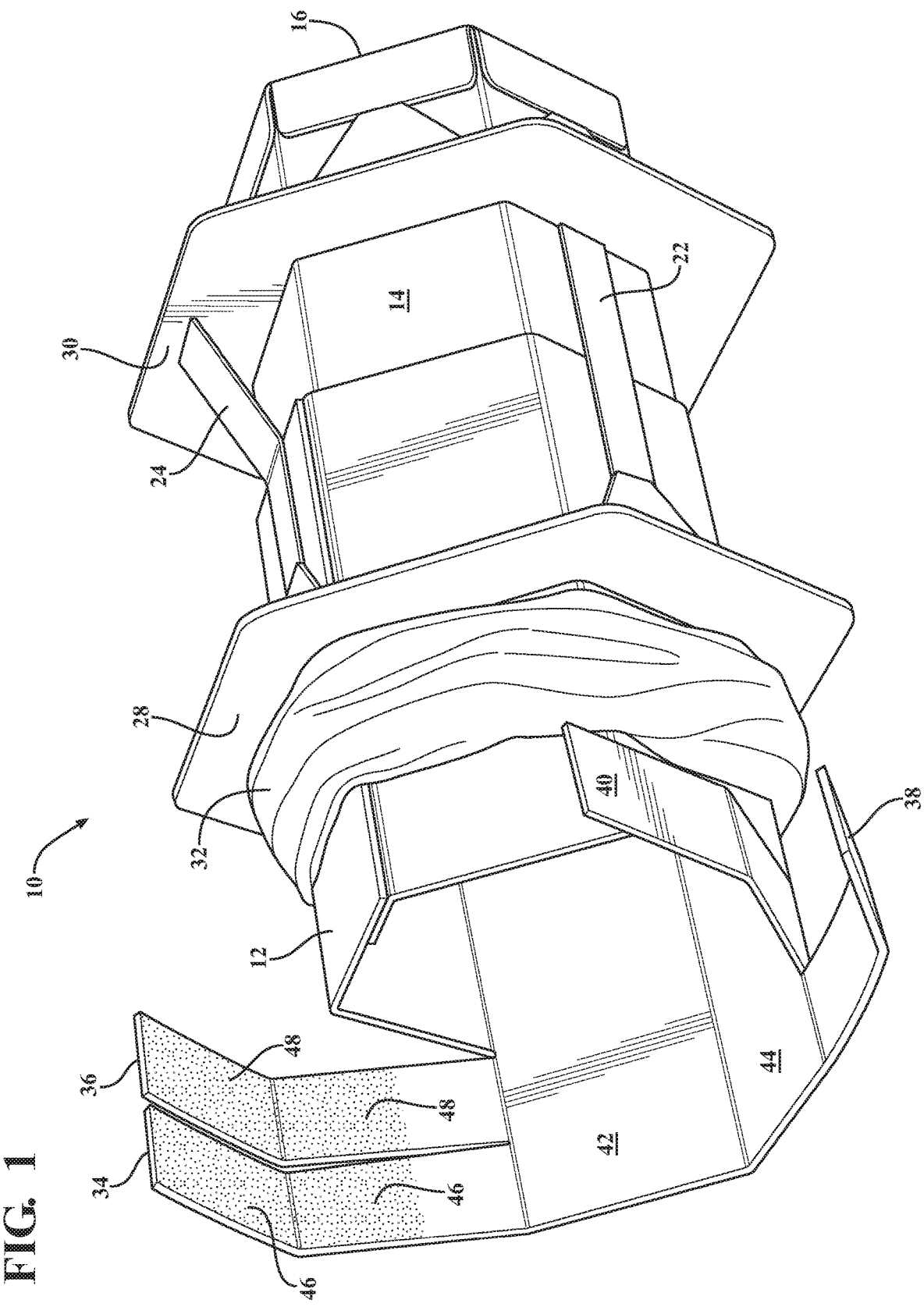
FIG. 1 is a perspective view of the forensic limb enclosure according to one non-limiting embodiment of the present inventions and in which the open interior and fabric drawstring is positioned upon an exterior circumferential supporting location of the elongated and length adjustable enclosure body, the pluralities of circumferential integrated and extending adjustable strap attachments also being shown and which are adapted to adjust to a secure holding circumference of the decedent's forearm or the like during axial insertion of the hand toward the closed interior end of the enclosure.

Referring first to FIG. 1, a perspective view of the forensic limb enclosure is generally depicted at 10 according to one non-limiting embodiment of the present inventions. The enclosure defines a body with a first portion 12 and a second portion 14, each being constructed of a closed tubular configuration (defined as any circular or polygonal shaped portion not limited to a hexagonal cross sectional configuration as shown) and having a specified axial length. The first portion 12 is open at a forward inserting end (such as for receiving a detached hand and forearm limb associated with a crime scene) with the second inter-engaged portion 14 exhibiting an opposite closed end 16.

In one non-limiting application, the body is constructed of a rigid paperboard, such as which can be internally lined with a Kraft paper. As is further known, Kraft paper or paperboard (cardboard) is produced from chemical pulp produced in the Kraft process, which is a process for conversion of wood into wood pulp, which consists of almost pure cellulose fibers, the main component of paper. In this fashion, the bags are breathable as needed to avoid premature contamination of the organic and other DNA evidence contained therein, such including protection from any of air, moisture, dust and dirt. Other non-limiting variants may include constructing the expandable body from a plasticized or plastic composite material (such including a sanitary plastic) and which can be interiorly lined with Kraft paper material.

Figure 3:
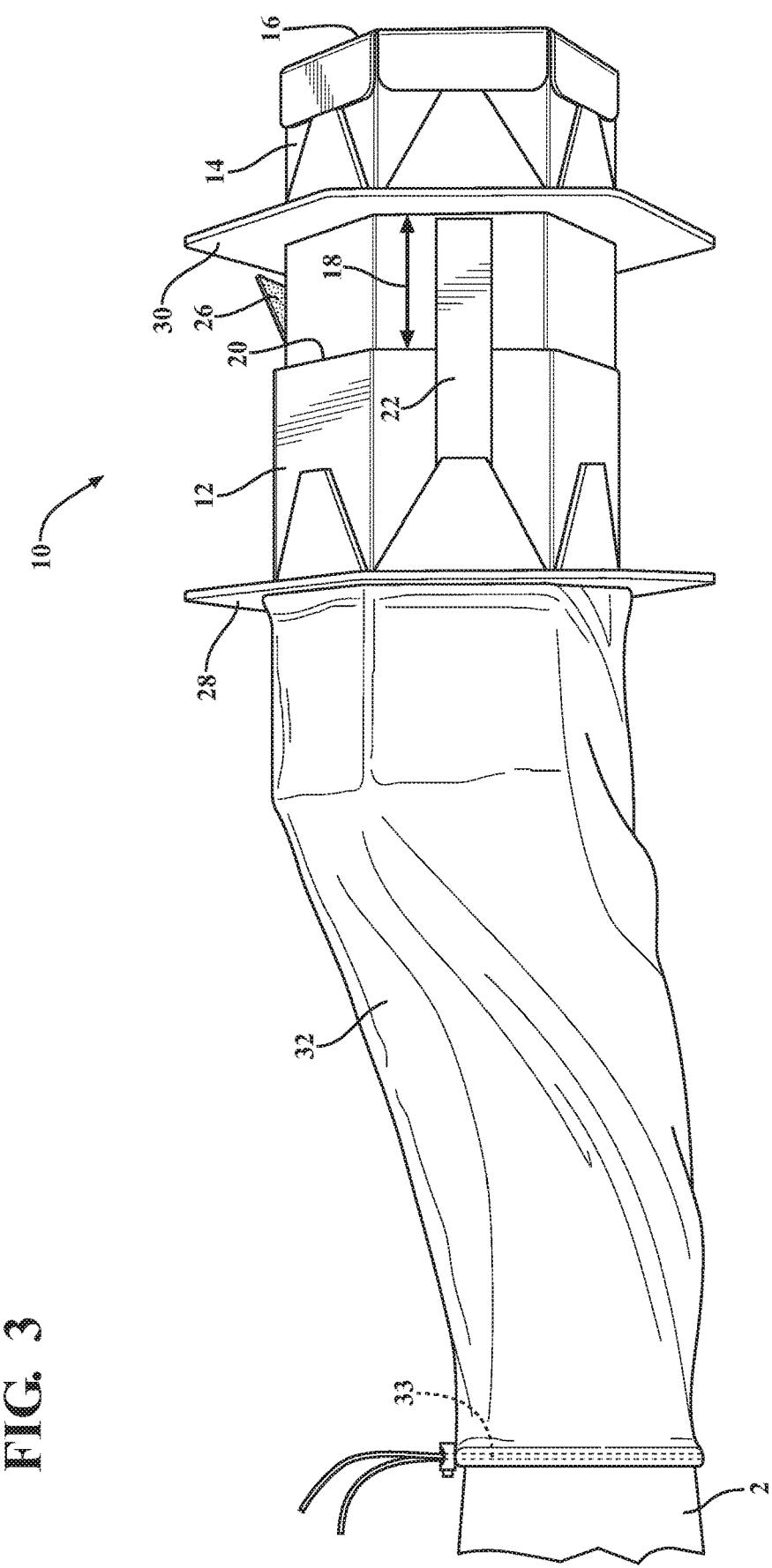
FIG. 3 is a side view of the enclosure and depicting the partial insertion of a limb into the open end thereof with drawstring extended over, the enclosure further exhibiting the axial length inter-adjustability provided by the telescoping nature of first and second inter-displaceable portions, additional fixing tabs being shown for fixing the enclosure in a desired length extended configuration corresponding to the dimensions of the limb being inserted therein.
Figure 4:
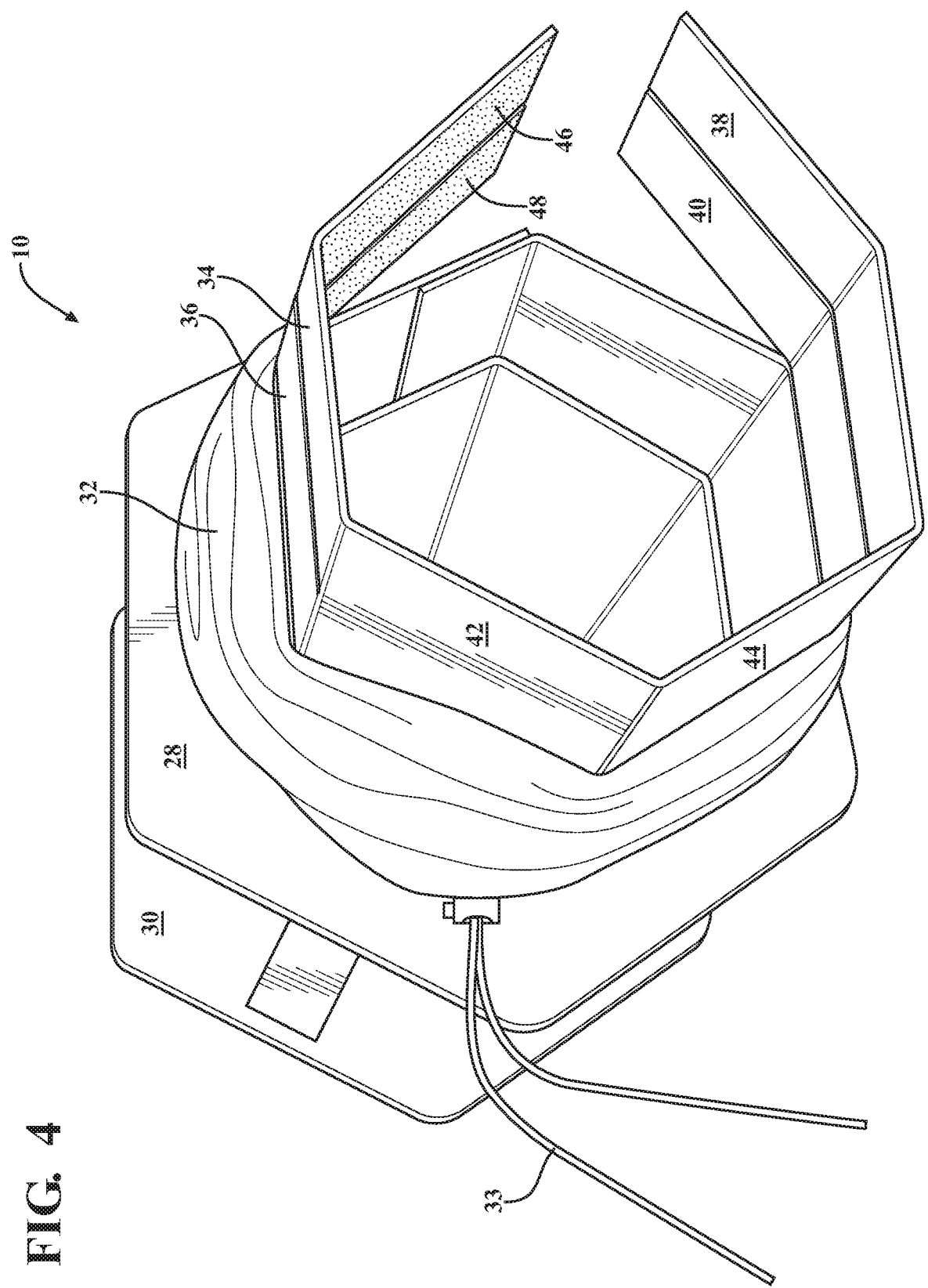
FIGS. 4-7 present a series of progressive installation illustrations of the limb enclosure for receiving and enclosing a (severed) limb in DNA safeguarding fashion.
Figure 5:
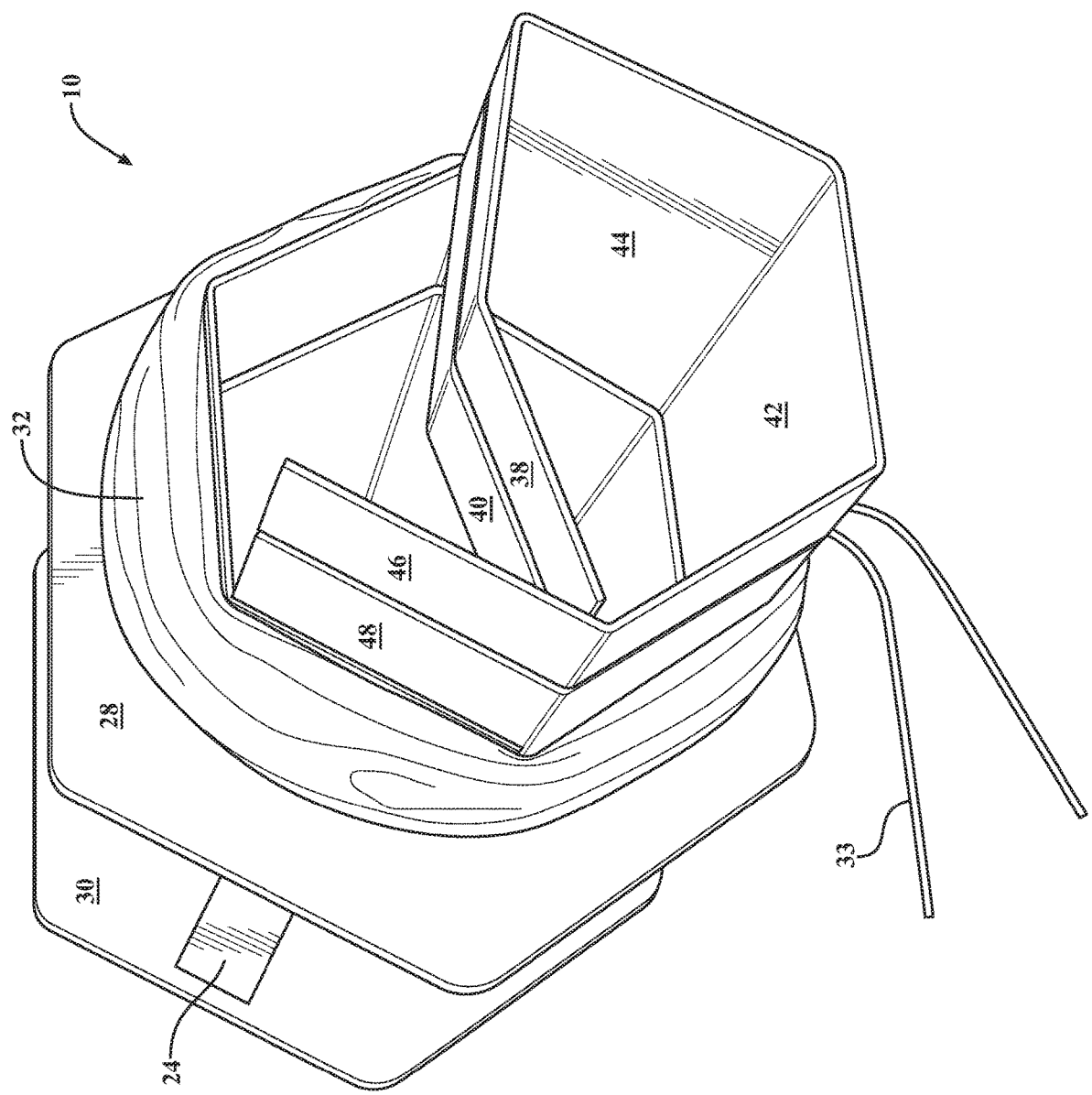
Figure 6:
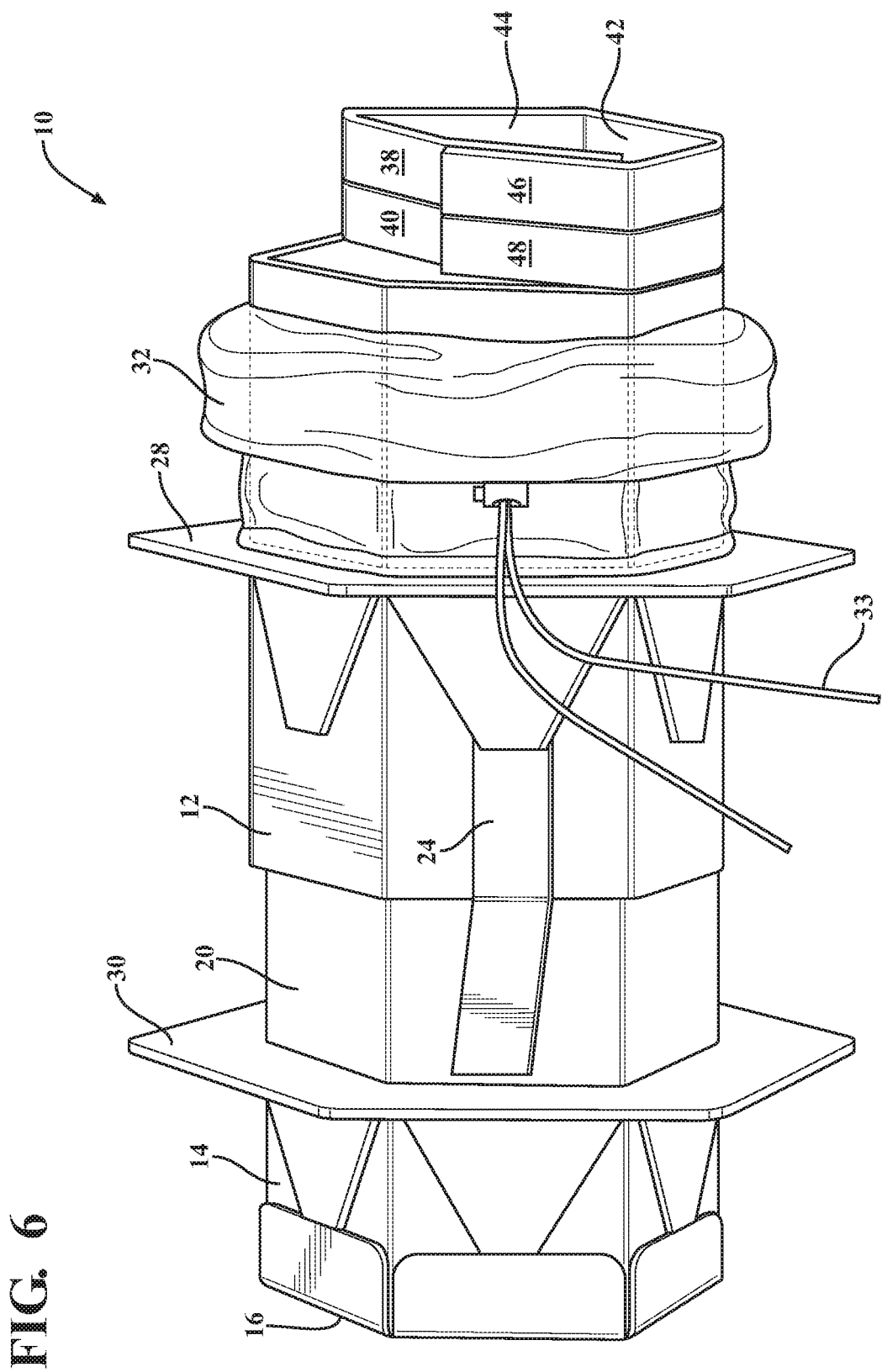
Figure 7:
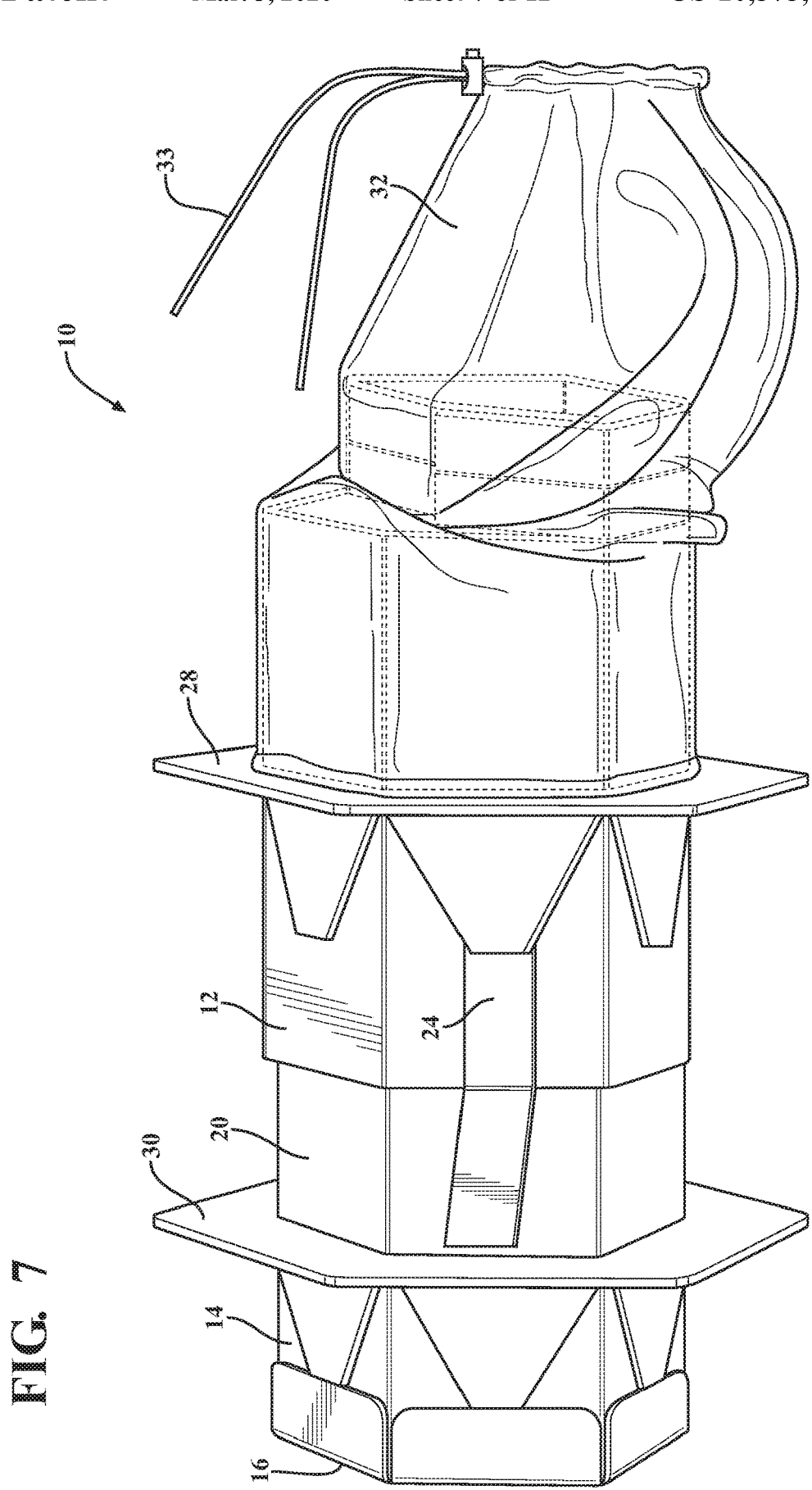

As further best shown in FIG. 3, the respective cross sectional profiles of the portions 12 and 14 are dimensioned with slight variances (with the first portion 12 being slightly greater in diameter for slidably receiving a forward inserting perimeter profile of the second portion 14) and so that the second portion can frictionally slide in bi-directional fashion (see arrow 18) both in and out of an interface boundary 20 between the overlapping telescoping portions 12/14. The range of axial telescoping adjustment is limited by the amount of overlap between the inserted perimeter of the second portion 14 and the outer receiving perimeter 12 of the first portion 12.

A plurality of axial extending length fixing straps 22, 24, et seq. are provided which extend from the first body portion 12 in overlapping fashion across the interface line 20 and in surface contact with the exterior of the second portion 14. The straps 22, 24, such as which can also include a paperboard material, also include inner surface peel away strips which reveal adhesive locations, see in underside hidden phantom representation at 26 in FIG. 3. In this fashion, and upon the telescoping portions 12 and 14 being inter-adjusted to a desired overall length corresponding to that necessary to receive the DNA containing hand/forearm, the underside peel away strips (not shown) are removed and the straps secured in place to establish a desired overall length of the portions 12/14 and to prevent subsequent inter-displacement between the portions 12/14.

Additional features include the provision of perimeter stand-off rims/flanges 28 and 30 associated with each of the telescoping portions 12 and 14, the stand-off flanges spacing the main telescoping bodies 12/14 above a ground surface or the like upon which the enclosure can be supported, such as during the evidence gathering/storage protocol. As will be described in further detail, the stand-off rims or flanges 28/30 can be either permanently affixed to the telescoping portions (such as integrated into the assembled blanks) or can be separately attached by any of adhesives, hook and loop fasteners, tab and slot configurations or the like.

An open interior and elongated fabric 32 (e.g. such as having a sleeve shape) is provided with a drawstring and defines an elongated shape with first and second open ends, a first of which is illustrated in supported fashion upon the first telescoping portion 12, and against an inside surface of the associated extending standoff rim 28. The fabric 32 with end positioned tightening drawstring (see at 33 in FIG. 3) includes an elongated body and, prior to inserting the hand and forearm (see at 2) into the open end of the enclosure, is positioned upon an exterior circumferential supporting location of the elongated and length adjustable enclosure body.

Figure 2:
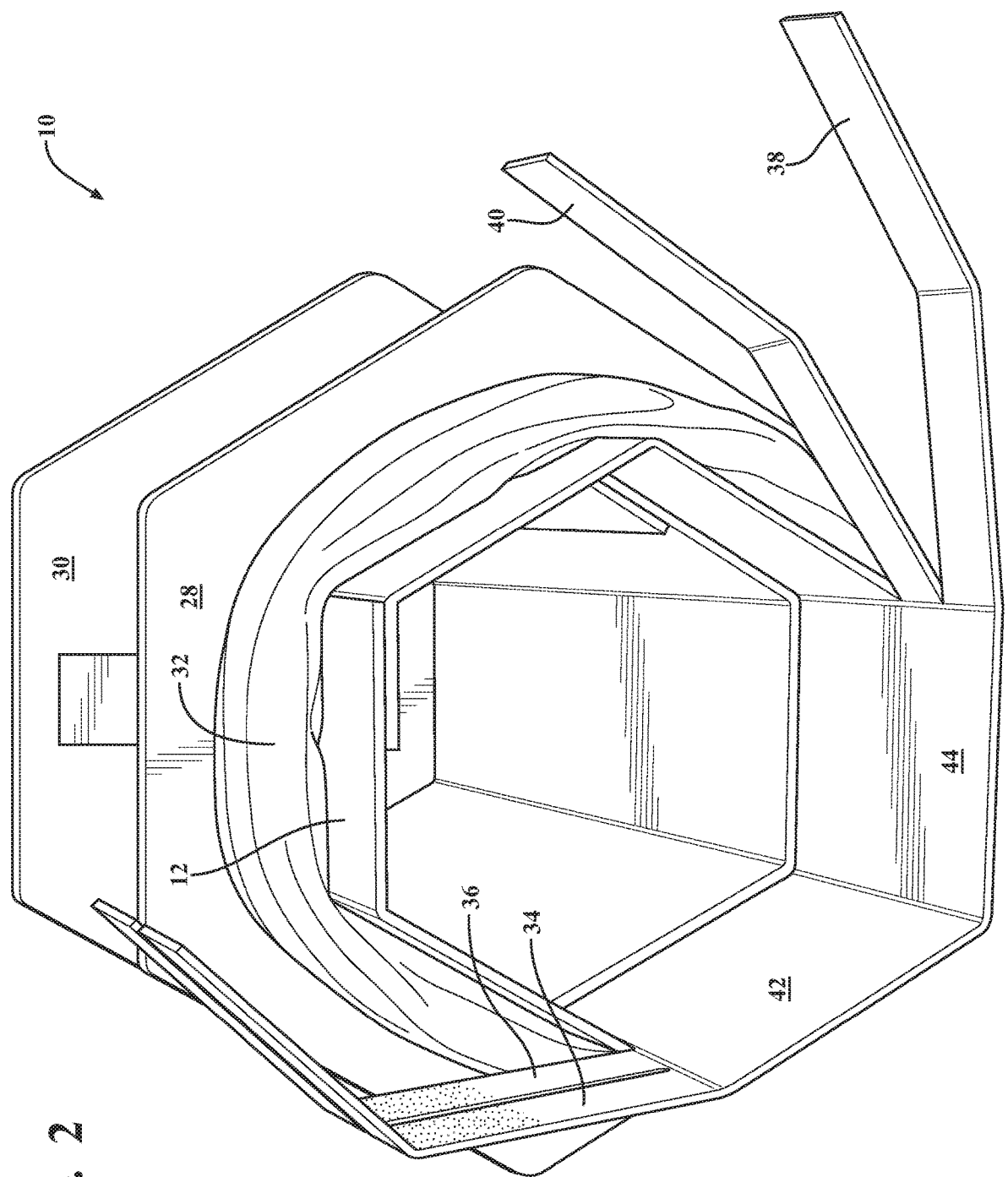
FIG. 2 is a rotated end view of the forensic limb/hand enclosure of FIG. 1.

Also shown are pluralities of circumferential integrated and extending adjustable strap attachments, see at 34/36 and 38/40 in each of FIGS. 1-2, which extend from the inner opposing end of the first enclosure portion 12 (see also base portion defined by the pair of indicated and interconnected hex panels 42/44 from which the pairs of strap attachments extend in opposing and circumferentially encircling fashion). Inner surfaces of a selected one of the pairs of width adjustable attachments (see at 46 and 48 as indicated in FIG. 1) can also include adhesives, such as which can be accessed through the use of additional peel-away strips, and to that, upon inserting the hand and lower forearm into the length adjusted enclosure, the pairs of circumferential straps are adjusted to securely fasten the enclosure to the location of the (upper) forearm projecting from its upper open end.

As further depicted in the side view of FIG. 3, insertion of the limb 2 into the open end thereof of the enclosure is succeeded by the extension of the drawstring extended over the limb (such as further may be removed from the body of a victim or suspect or which may remain attached to the decedent). At this point, the encased limb is transported to a crime or DNA lab or the like, prior to removal and in order to process the evidence in a secure environment.

Figure 8:
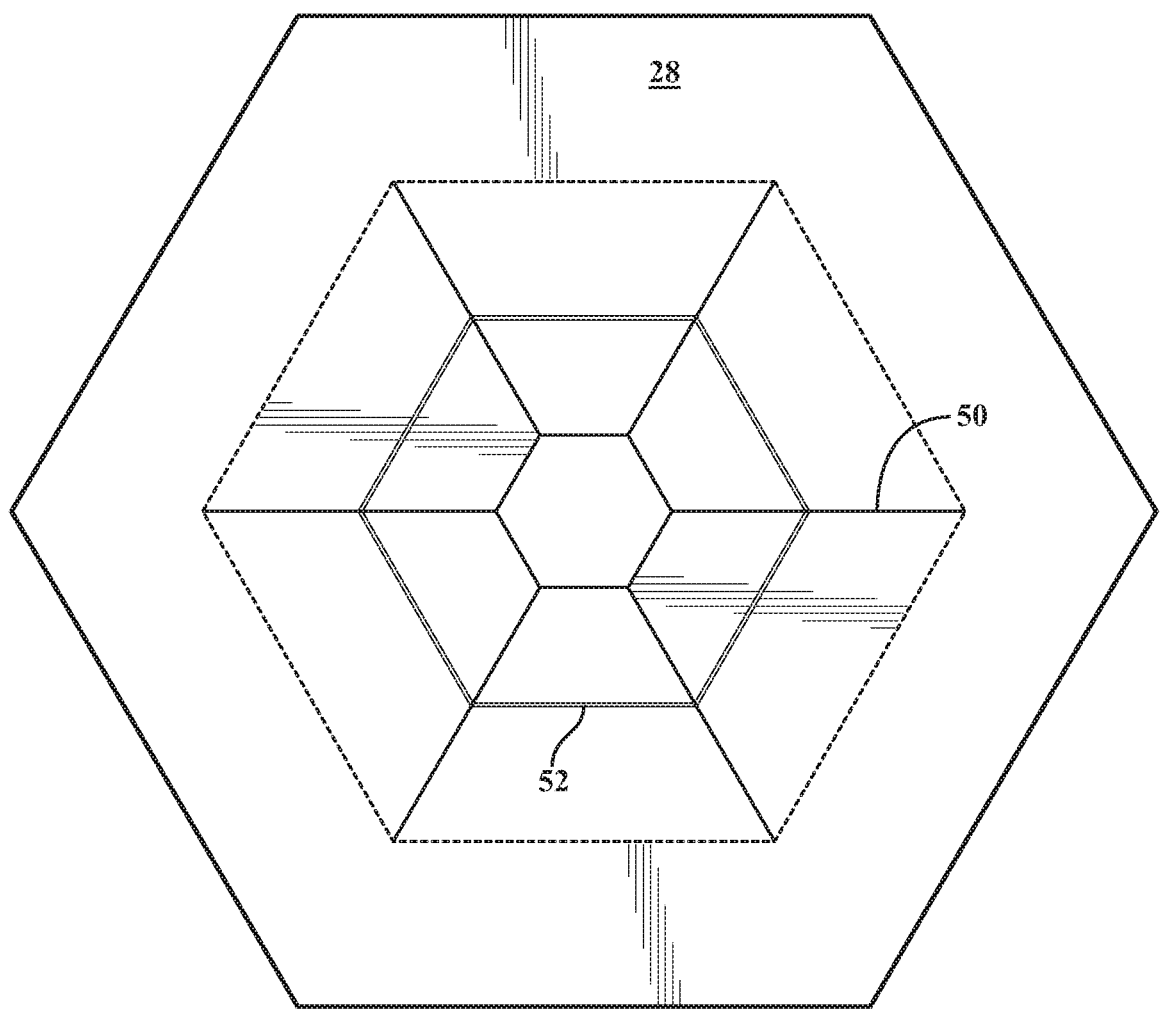
FIGS. 8-10 are a series of schematic views of the blank constructions associated with the limb (forearm/hand) enclosure.
Figure 9:
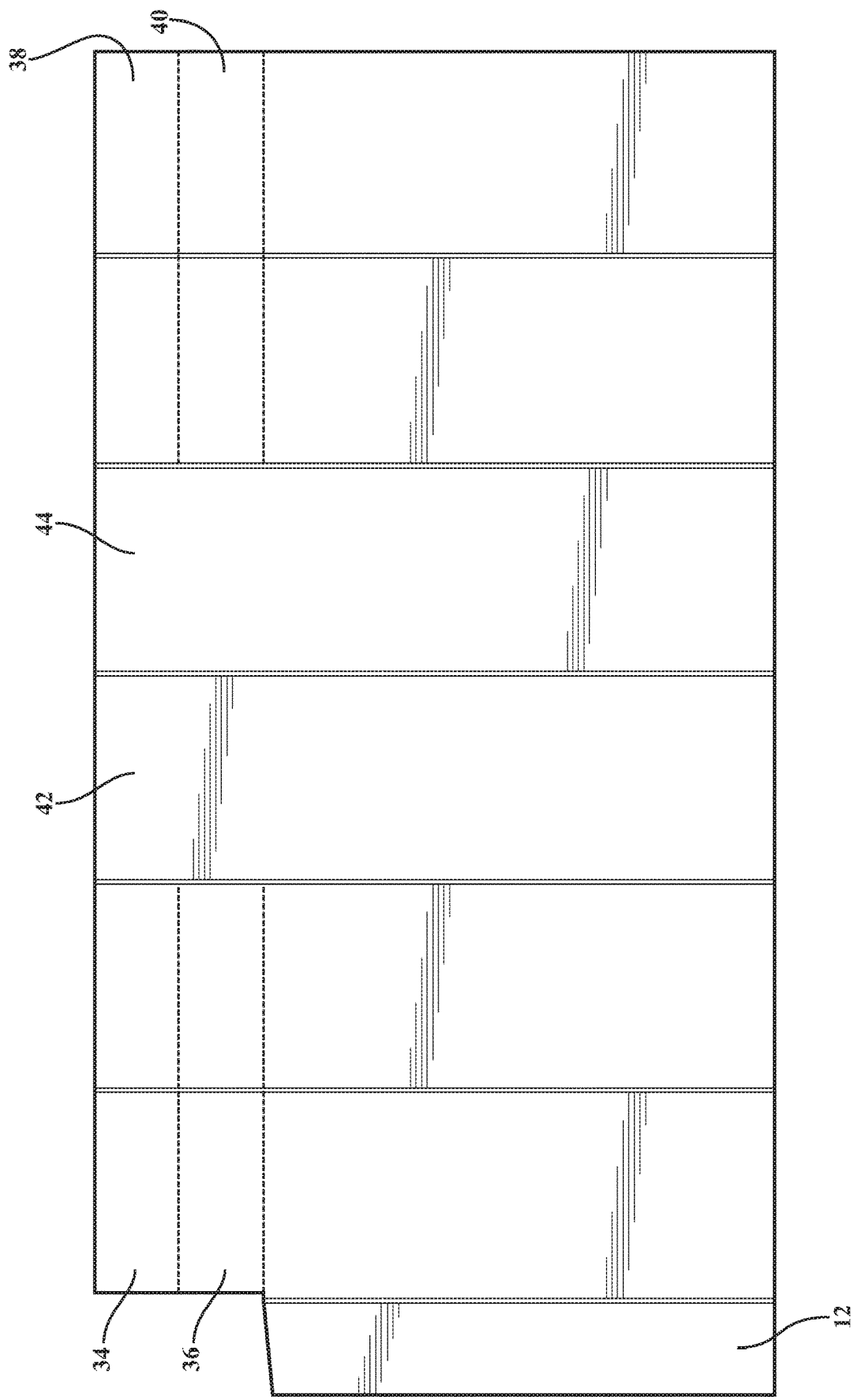
Figure 10:
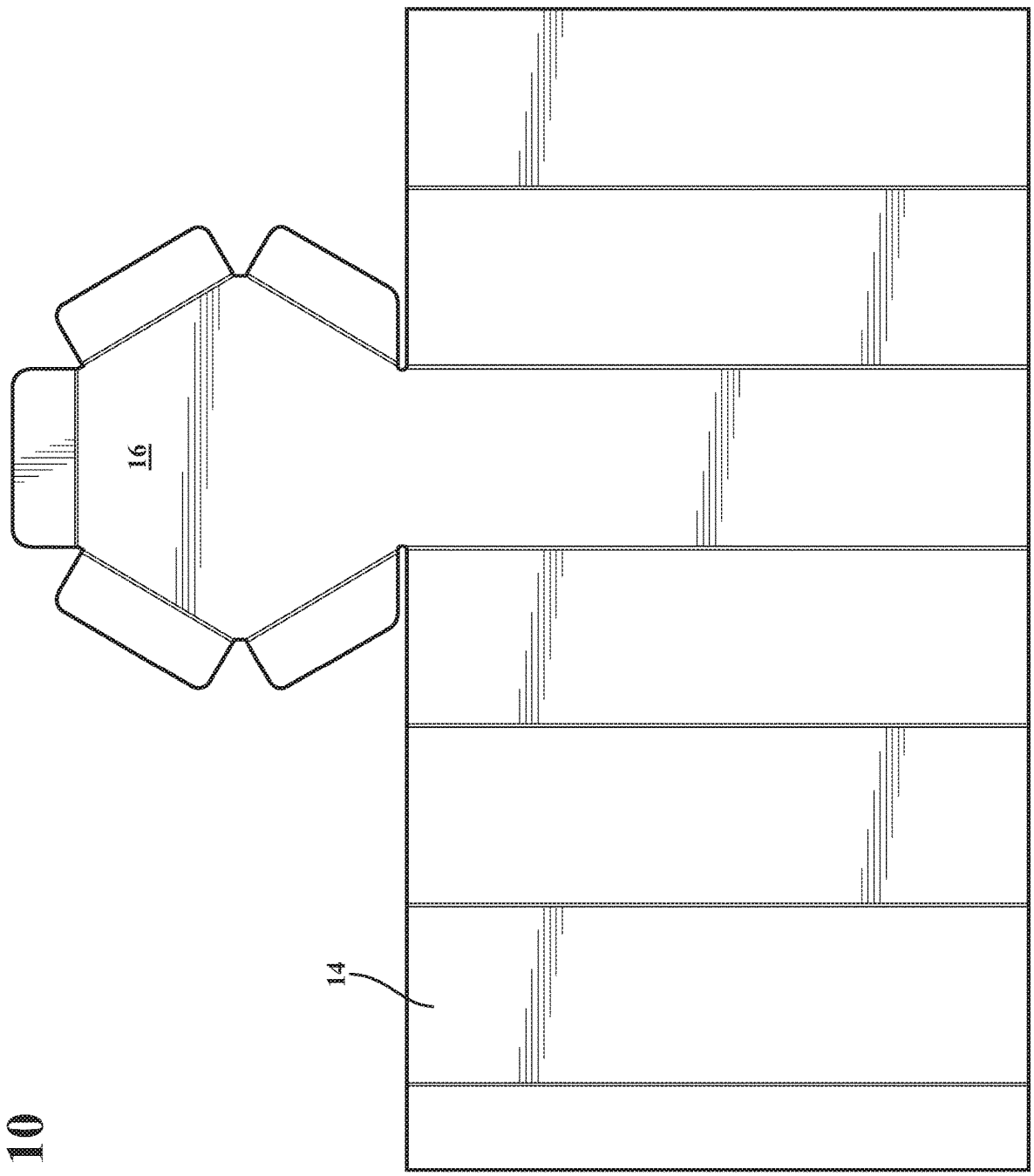

With further reference to FIGS. 4-7, presented are a series of progressive installation illustrations of the limb enclosure for receiving and enclosing a (severed) limb in DNA safeguarding fashion, such according to one non-limiting protocol for receiving, closing and tagging an evidence entrained limb in DNA protecting fashion. FIGS. 8-10 further provide a series of schematic views of the blank constructions associated with the limb (forearm/hand) enclosure and pertaining to the first 12 and second 14 individual portions prior to configured assembly in the manner shown in FIGS. 1-3.

This includes a cutaway plan view of an assembled blank in FIG. 8 depicting each of cut 50 and crease 52 lines associated with either of the main inter-telescoping sections and according to one non-limiting arrangement. Also depicted are a pair of unfolded blank views corresponding to the unfolded first portion 12 (FIG. 9) and second portion 14 (FIG. 10), each of these depicting the multiple and inter-foldable panels which collectively define the hex polygonal or other desired cross sectional shape of each inter-fitting telescoping portion. Without limitation, the stand off rims or spacers 28 and 30 can also be provided as separate slide-on or adhesively attachable portions (see as described below with reference to FIGS. 11-12).

Additional features include the evidence enclosures being pre-printed with informational fields necessary for proper evidence submission to all crime laboratories, including such as a chain of custody section. Other variants of the limb receiving evidence enclosure can include the body being reconfigured to provide a single elongated and tubular receiving portion as opposed to having first 12 and second 14 inter-telescoping portions.

This can also include providing the enclosure as a single unitary and elongated body with such as additional breakaway portions or reducing its overall length (such contemplating length reducing perforations in circumferentially spaced iterations at its remote end, such which can remain open until appropriately length sized and prior to receiving a separately attachable end cap. The evidence enclosure can further be reconfigured for receiving other types of limbs (including legs, feet etc.) in additional envisioned variants.

Figure 11:
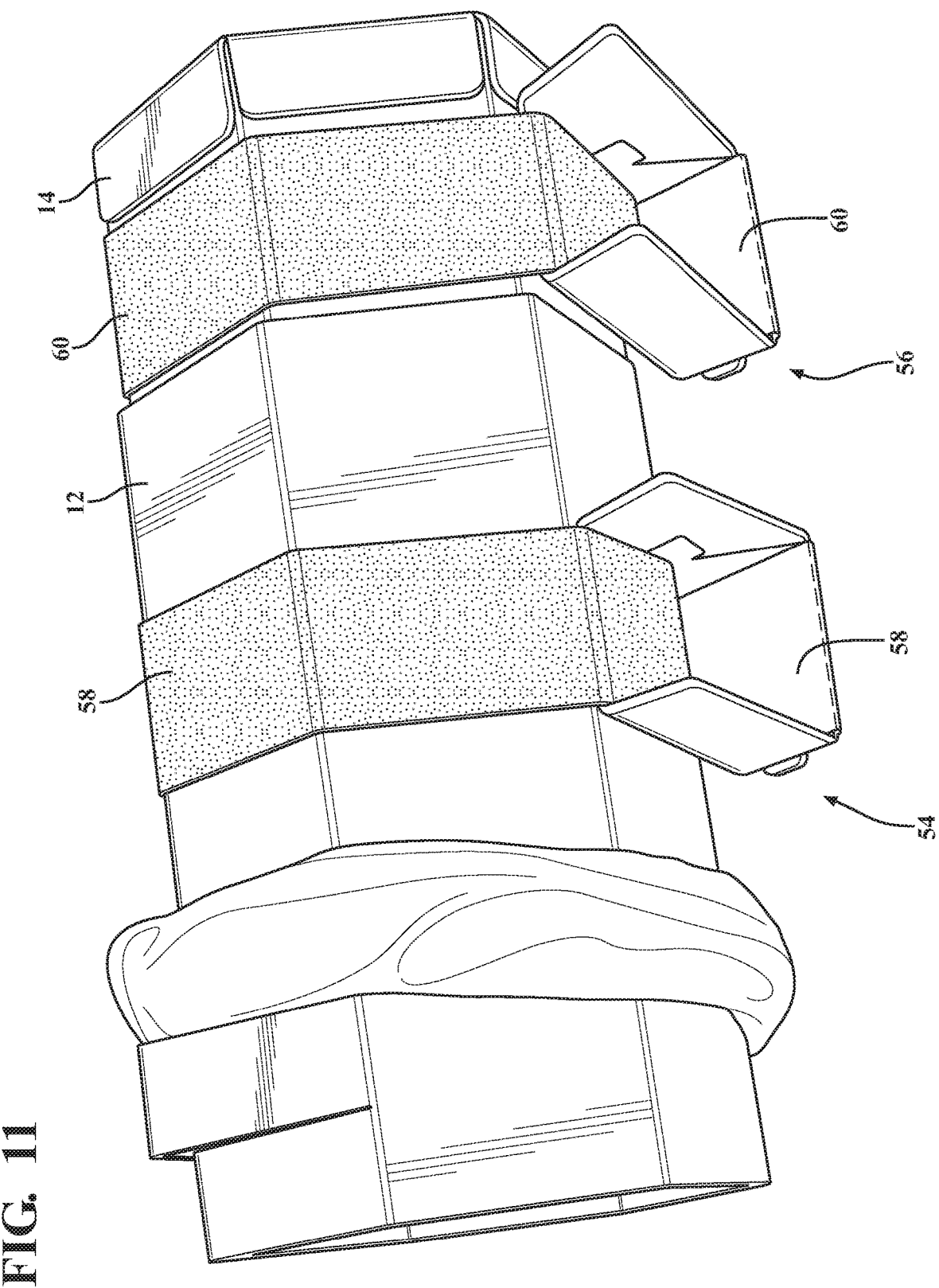
FIG. 11 is an illustration of an alternate form of stand off spacer or rim attachment defining a separate assembly and secured to a main body portion via a hook and loop band attachment.

Referring to FIG. 11, an illustration is shown of an alternate form of stand off spacer or rim attachment, see pair at 54 and 56, each of which defining a separate assembly secured to each of the telescoping main body portions 12 and 14, such as via hook and loop band attachments 58 and 60. As further depicted in the FIG. 12, a blank illustration is provided of selected stand off attachment 54 of FIG. 11 and which includes a plurality of inter-folding panels which assemble to create a cradling three sided cross sectional support profile.

Figure 12:
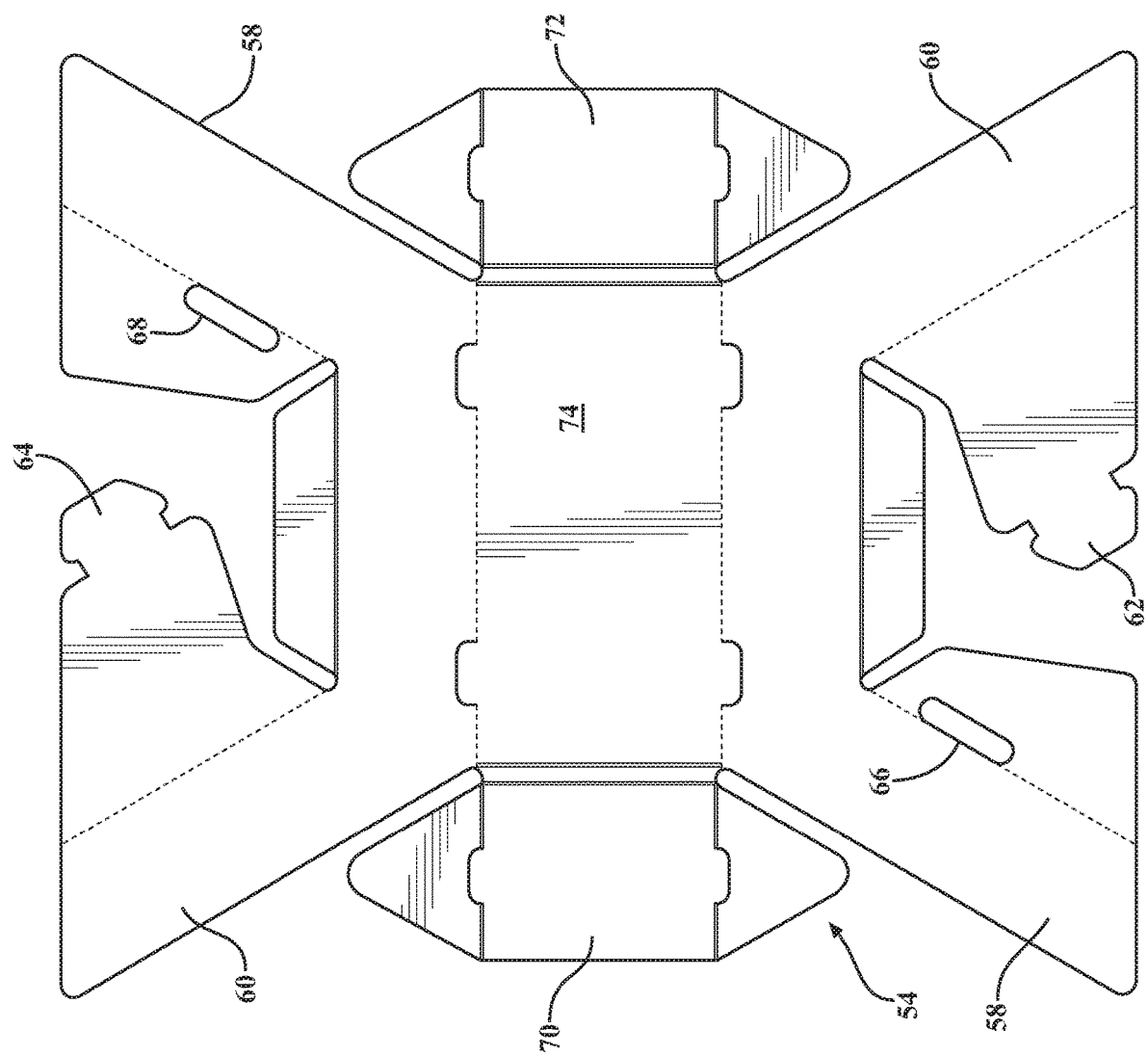
FIG. 12 is a blank illustration of the stand off attachment of FIG. 11.

The panels further assemble to provide each attachable stand-off spacer with inner and outer linearly spaced ledges (these shown at 58 and 60 for selected spacer attachment 54 in FIG. 11 and further including opposite pairs of inter-folding panels 58/60 and 58'/60' in FIG. 12). As further shown in FIG. 12, the blank construction of the spacer attachment further includes tabs 62/64 and slots 66/68 for inter-assembling the pairs of support ledges 58/60 and 58'/60', as well as a pair of fold-in supports 70 and 72 which interconnect to ends of a common base panel 74 also supporting the stand off ledges. Without limitation, the present design includes any version of a stand-off spacer configuration (permanent or attachable) beyond that shown.

The present invention accordingly provides an effective forensic style glove or covering which elevates the DNA or evidence contaminated limb (such as also including gunshot residue or the like) to allow for securing key evidence up off of the ground and out of any of debris, dirt, mud, snow rain or other foreign contaminants (the draw sting attachment extending over the forearm providing additional contamination prevention support). An additional feature of the assembly is that it permits the removal of the stand-off attachments as shown in FIGS. 11-12, such as in order to permit the assembly 10 to be placed within a body bag along with the remainder of the corpse.

Additional to the paperboard and Kraft paper constructions previously described, it is again understood that the contamination preventative and limb support assembly can also be stored prior to use in any type of rigid or flexible sanitary container, such being enabled for rapid deployment in the field. The main body portions of the forensic enclosure can further include any type of fabric (cotton) or other interior lining to further assist in capturing, containing, preserving and protecting the evidence, thereby maintaining its integrity for use at trial.

Having described my invention, other and additional preferred embodiments will become apparent to those skilled in the art to which it pertains, and without deviating from the scope of the appended claims:

I claim:

1. A forensic enclosure for preserving DNA evidence on a limb of a subject, comprising:
   first and second telescopically adjustable portions constructed of a rigid paperboard which, upon being slidably assembled to one another, establishing an open interior accessible from a first open end and adapted to receive the inserted limb up to a second closed end;
   standoffs located upon an exterior of each of said adjustable portions adapted to elevate the limb above a ground surface; and
   said first adjustable portion including a panel extending beyond said open end, circumferential directed straps extending from opposite length extending edges of said panel so that said straps are adapted to encircle a circumference of the limb, said straps having adhesives at opposing and overlapping ends which, upon adjusting to a circumference of the limb, are affixed to retain position of said body over the limb.

2. The forensic enclosure of claim 1, said first and second telescopically adjustable portions each further comprising a hexagonal configuration.

3. The forensic enclosure of claim 1, further comprising an interior lining applied to each of said first and second telescopically adjustable portions.

4. The forensic enclosure of claim 1, further comprising an elongated and sleeve shaped fabric attached at an inner end to said first telescopically adjustable portion, said fabric adapted to be extended to cover an additional portion of the limb, a drawstring extending from an outer end of the fabric and, upon tightening, enclosing around the limb.

5. The forensic enclosure of claim 1, further comprising additional fixing straps extending axially across an interface edge between said first and second telescopically adjustable portions.

6. The forensic enclosure of claim 5, further comprising said fixing straps being secured to said first telescopically adjustable portion and including additional adhesives for engaging said second telescopically adjustable portion.

7. The forensic enclosure of claim 5, said circumferential directed straps and said axial directed fixing straps each further comprising a paperboard material.

8. The forensic enclosure of claim 7, said circumferential directed straps each further comprising hinge defining intermediate locations.

9. The forensic enclosure of claim 1, said standoffs further comprising radially projecting portions extending circumferentially from outer rim locations of each of said adjustable portions.

10. The forensic enclosure of claim 1, said standoffs further comprising separately attachable portions secured to said telescopically adjustable portions by hook and loop band attachments respectively looped about a circumference of each adjustable portion.

11. The forensic enclosure of claim 1, further comprising said first and second telescopically adjustable portions each being initially provided as a flattened blank exhibiting multiple crease lines for reconfiguring into a multi-sided polygonal configuration.

12. The forensic enclosure of claim 11, said flattened blanks each further comprising additional crease lines and cut lines for said standoffs to extend from the polygonal configuration.

13. The forensic enclosure of claim 1, said panel extending from said first adjustable portion further comprising a pair of hinged panels.

14. A forensic enclosure for preserving DNA evidence on a limb of a subject, comprising:
    first and second telescopically adjustable portions which, upon being slidably assembled to one another, establishing an open interior accessible from a first open end and adapted to receive the inserted limb up to a second closed end;
    an elongated and sleeve shaped fabric attached at an inner end to said first telescopically adjustable portion, said fabric adapted to be extended to cover an additional portion of the limb, a drawstring extending from an outer end of the fabric and, upon tightening, enclosing around the limb;
    standoffs located upon an exterior of each of said adjustable portions adapted to elevate the limb above a ground surface; and
    said first adjustable portion including a panel extending beyond said open end, circumferential directed straps extending from opposite length extending edges of said panel so that said straps are adapted to encircle a circumference of the limb, said straps having adhesives at opposing and overlapping ends which, upon adjusting to a circumference of the limb, are affixed to retain position of said body over the limb.

15. A forensic enclosure for preserving DNA evidence on a limb of a subject, comprising:
    first and second telescopically adjustable portions which, upon being slidably assembled to one another, establishing an open interior accessible from a first open end and adapted to receive the inserted limb up to a second closed end;
    standoffs located upon an exterior of each of said adjustable portions adapted to elevate the limb above a ground surface;
    said first adjustable portion including a panel extending beyond said open end, circumferential directed straps extending from opposite length extending edges of said panel so that said straps are adapted to encircle a circumference of the limb, said straps having adhesives at opposing and overlapping ends which, upon adjusting to a circumference of the limb, are affixed to retain position of said body over the limb; and
    additional fixing straps extending axially across an interface edge between said first and second telescopically adjustable portions.

* * * * *